(12) United States Patent
Batchelor et al.

(10) Patent No.: US 9,144,454 B2
(45) Date of Patent: Sep. 29, 2015

(54) ELECTROSURGICAL COLPOTOMY DEVICE

(71) Applicant: GYRUS ACMI, INC., Southborough, MA (US)

(72) Inventors: Kester J. Batchelor, Mound, MN (US); Nikhil M. Murdeshwar, Maple Grove, MN (US); Tracey L. Dobbs, Delano, MN (US); Jyue Boon Lim, New Brighton, MN (US); Tsuyoshi Hayashida, Maple Grove, MN (US); Riyad Moe, Waunakee, WI (US)

(73) Assignee: GYRUS ACMI, INC., Southborough, MA (US)

( * ) Notice: Subject to any disclaimer, the term of this patent is extended or adjusted under 35 U.S.C. 154(b) by 86 days.

(21) Appl. No.: 14/077,367

(22) Filed: Nov. 12, 2013

(65) Prior Publication Data

US 2015/0133923 A1 May 14, 2015

(51) Int. Cl.
*A61B 18/14* (2006.01)
*A61B 17/42* (2006.01)
(Continued)

(52) U.S. Cl.
CPC .............. *A61B 18/14* (2013.01); *A61B 17/4241* (2013.01); *A61B 18/1482* (2013.01); *A61B 18/1485* (2013.01); *A61B 2017/00287* (2013.01); *A61B 2018/00559* (2013.01); *A61B 2018/00601* (2013.01); *A61B 2018/141* (2013.01); *A61B 2018/1407* (2013.01)

(58) Field of Classification Search
CPC .................. A61B 18/1485; A61B 2018/00559; A61B 2018/1407; A61B 2018/141; A61B 2018/142; A61B 2017/4216; A61B 2017/4225

USPC ............................... 606/48, 50, 119; 607/138
See application file for complete search history.

(56) References Cited

U.S. PATENT DOCUMENTS 4,775,362 A   10/1988   Kronner
5,209,754 A    5/1993   Ahluwalia
(Continued)

FOREIGN PATENT DOCUMENTS

DE   10 2009 018 521 A1   10/2010
EP       2 243 437 A1      10/2010
WO       2013/075103 A1     5/2013

OTHER PUBLICATIONS

Con Med: VCare Device, Marketing Brochure, Jun. 2010, Utica, NY.
(Continued)

*Primary Examiner* — Michael Peffley
*Assistant Examiner* — Thomas Giuliani
(74) *Attorney, Agent, or Firm* — Oliff PLC

(57) ABSTRACT

A bipolar electrosurgical colpotomy device includes a colpotomy cup and a tissue containment bag. The colpotomy cup includes a first electrode located adjacent to a rim of the cup, the rim being configured to contact an internal surface of a patient's cervico-vaginal junction. The tissue containment bag includes an opening and a second electrode located adjacent to the opening. The tissue containment bag is configured to surround the patient's uterus and the opening is configured to fit over an external surface of the patient's cervico-vaginal junction. Applying a voltage potential between the first and second electrodes vaporizes tissue at the patient's cervico-vaginal junction by electrosurgical energy passing through the tissue disposed between the first and second electrodes. The tissue containment bag then can be used to remove the uterus from the patient, possibly after masticating the uterus within the bag.

9 Claims, 10 Drawing Sheets

(51) Int. Cl.
*A61B 18/00* (2006.01)
*A61B 17/00* (2006.01)

(56) References Cited

U.S. PATENT DOCUMENTS

| | | | |
|---|---|---|---|
| 5,234,439 | A | 8/1993 | Wilk et al. |
| 5,341,815 | A | 8/1994 | Cofone et al. |
| 5,520,698 | A | 5/1996 | Koh |
| 5,569,284 | A | 10/1996 | Young et al. |
| 5,643,285 | A | 7/1997 | Rowden et al. |
| 5,759,187 | A | 6/1998 | Nakao et al. |
| 5,840,077 | A | 11/1998 | Rowden et al. |
| 5,997,547 | A | 12/1999 | Nakao et al. |
| 6,537,273 | B1 | 3/2003 | Sosiak et al. |
| 7,806,894 | B1 | 10/2010 | Rosenblatt et al. |
| 8,192,444 | B2 * | 6/2012 | Dycus ................ 606/113 |
| 2001/0021854 | A1 | 9/2001 | Donnez et al. |
| 2004/0102770 | A1 | 5/2004 | Goble |
| 2007/0027450 | A1 | 2/2007 | Nezhat et al. |
| 2009/0192510 | A1 | 7/2009 | Bahney |
| 2012/0109124 | A1 * | 5/2012 | Morozov ................ 606/46 |
| 2012/0323079 | A1 | 12/2012 | Bakare et al. |

OTHER PUBLICATIONS

Cooper Surgical: Koh Cup, Marketing Brochure, Oct. 2006, Trumbull, CT.
Cooper Surgical: Uterine Manipulator, Marketing Brochure, Feb. 2008, Trumbull, CT.
Dec. 23, 2014 Search Report and Written Opinion issued in International Application No. PCT/US2014/060125.

\* cited by examiner

ELECTROSURGICAL COLPOTOMY DEVICE

BACKGROUND

This disclosure relates to surgical instruments, and in particular to electrosurgical instruments utilized in total laparoscopic hysterectomy (TLH) procedures.

Electrosurgical instruments used to resect a patient's cervix from the vagina are known. Such instruments generally carry out a number of functions: positioning of the uterus for resection, maintaining pneumoperitoneum during tissue resection, aiding in physician visibility during resection, and incision and resection of a patient's cervix from the vagina. It is known to provide a colpotomy device having an electrosurgical element and a uterine manipulator to aid in incising and positioning the uterus for resection.

In general, the incision and resection are performed by a single electrosurgical instrument. This is typically introduced laparoscopically into the abdomen through a trocar or other similar device.

It is also known for the incision and resection to be performed by two electrosurgical instruments. Although one electrosurgical instrument may be introduced vaginally, at least one other electrosurgical instrument is typically introduced laparoscopically into the abdomen through a trocar or other similar device.

Instead of an electrosurgical instrument, mechanical cutting instruments such as scissors are sometimes used to form the incision.

Some known electrosurgical instruments make use of a colpotomy cup in order to position and manipulate the uterus for resection. These can take many forms, but generally have a leading edge which fits at or near the cervico-vaginal junction. Colpotomy cups sometimes also carry a monopolar electrosurgical cutting instrument, either attached to the cup, or attached to another apparatus located near the patient's uterus.

Monopolar devices exist for performing the incision to sever the cervix from the vagina. A first or "active" electrode performs the cutting in these configurations, with a second or "return" electrode placed elsewhere on the body.

In addition to resection of the patient's cervix from the vagina, the uterus, once resected, must be removed from the patient's pelvis. In TLH procedures, the uterus is often removed vaginally.

SUMMARY

As mentioned above, some electrosurgical devices used in TLH procedures make use of monopolar electrosurgical elements. Monopolar electrosurgical elements are used with a separate return electrode (for example, a return pad, grounding patch or neutral electrode) that is placed some distance away from the incision site. As a result of the distance between the return electrode and the incision site, monopolar electrosurgical elements typically exhibit poorer control over application of energy to the incision site. In particular, monopolar electrodes deliver less controllable pulses of energy and/or higher voltages, which can result in increased heat at the surgical site, and potentially damage other tissues, such as nerves, ureters or colon tissue near that site. A risk particular to TLH procedures is over-shortening of the vagina during resection of the cervix from the vagina. This can be caused, for example, by creating too much heat at the cutting device while performing the cervico-vaginal incision. Another complication related to creating too much heat during cutting is known as dehiscence. This occurs when the incised tissues that are brought together to close the vaginal canal with sutures during the procedure fail to fuse before the suture absorption period is reached. This is due to the heat damage to the tissue preventing the desired healing.

A bipolar electrosurgical configuration reduces the risks associated with monopolar elements because a bipolar instrument has a shorter distance between the tissue to be excised and a "return" electrode. In other words, bipolar devices provide two (or more) electrodes that are close to each other and between which a voltage potential is applied that is suitable for vaporizing the tissue located between the electrodes. This enables the electrosurgical cutting energy to be more precisely focused. It also allows for lower cutting voltages to be used.

In order to overcome difficulties inherent to the TLH procedure, namely, difficulty of incision, thermal damage at the vaginal cuff and the risks of damaging other organs, overshortening the patient's vagina or risking future dehiscence, an aspect of the invention relates to a bipolar electrosurgical assembly that includes a colpotomy cup, a tissue containment bag, and two electrodes, a first one of which is located adjacent to the rim of the colpotomy cup, and a second one of which is located adjacent to the opening of the tissue containment bag. The rim of the colpotomy cup is configured to contact an internal surface of a patient's cervico-vaginal junction, the tissue containment bag is configured to surround the patient's uterus, and the opening of the tissue containment bag is configured to fit over an external surface of the patient's cervico-vaginal junction. Because the first and second electrodes will be disposed close to each other, the device will function as a bipolar electrosurgical device such that application of a voltage potential between the first and second electrodes vaporizes tissue at the patient's cervico-vaginal junction by electrosurgical energy passing through the tissue disposed between the first and second electrodes.

According to some embodiments, the second electrode completely encircles the opening of the tissue containment bag.

According to some embodiments, the first electrode completely encircles the rim of the colpotomy cup.

If an arrangement is provided in which the first electrode completely encircles the rim of the colpotomy cup and in which the second electrode completely encircles the opening of the tissue containment bag, a relatively large voltage potential will need to be applied between the two electrodes, which could be overly traumatic. Alternatively, if the voltage is not enough, by being spread out over the entire surface area of each electrode, the applied power could be insufficient to completely vaporize enough tissue to fully detach the uterus. It is thus preferable to have at least one of the electrodes (usually the electrode provided with the cup) be relatively small such that it does not completely encircle the cervicovaginal junction. In this case, the smaller electrode is moved around the cervico-vaginal junction during application of the electrosurgical energy so as to completely detach the uterus. Such an arrangement highly focuses the electrosurgical energy at a given area (corresponding to the small electrode) as the electrode is moved (rotated) around the cervico-vaginal junction.

According to some embodiments, the device includes a first shaft having a proximal end, a distal end and a uterine manipulator adjacent to the distal end of the first shaft, and a second shaft disposed over the first shaft and having a proximal end and a distal end, a proximal end of the colpotomy cup being attached to the distal end of the second shaft so that the colpotomy cup moves with the second shaft. In this arrangement, the second shaft can be rotatable around the first shaft so as to cause the first electrode to rotate around the cervico-vaginal junction. In particular, the first electrode would be located adjacent to only a portion of the rim (rather than encircling the rim) such that the second shaft and attached colpotomy cup are rotated around the first shaft in order to completely detach the uterus.

According to some embodiments, the device includes a spindle to which the first electrode is attached, and the spindle is rotatable about an axis of the second shaft independently of the colpotomy cup.

According to some embodiments, the device includes a second colpotomy cup disposed within the colpotomy cup having the first electrode, the colpotomy cup and the attached first electrode being rotatable relative to the second colpotomy cup. The second colpotomy cup thus maintains the uterus at the desired position during the procedure.

BRIEF DESCRIPTION OF THE DRAWINGS

Various exemplary embodiments of an electrosurgical colpotomy device according to aspects of the invention will be described in detail with reference to the following drawings in which.

DETAILED DESCRIPTION

The following exemplary embodiments are described below with reference to the figures in the context of female pelvic surgery, and in particular total laparoscopic hysterectomy (TLH).

Figure 1:
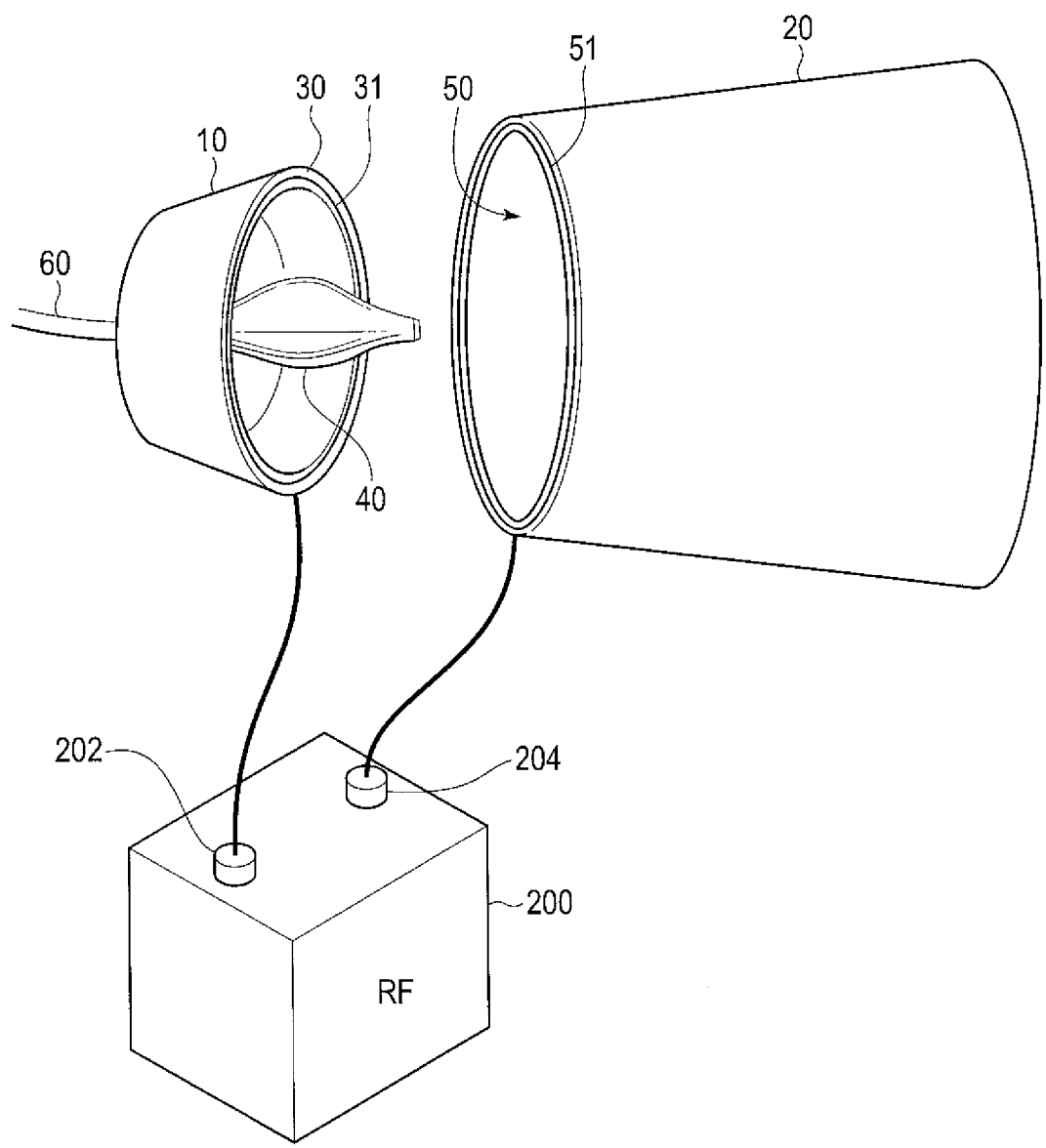
FIG. 1 is a perspective view of a system including a bipolar electrosurgical colpotomy device that incorporates a colpotomy cup, a tissue containment bag, and a uterine manipulator, with the cup and bag coupled to an electrosurgical energy generator.

FIG. 1 is a perspective view of a bipolar electrosurgical colpotomy device coupled to an electrosurgical energy generator 200. The bipolar electrosurgical colpotomy device includes a first shaft 60 that functions as a uterine manipulator, and terminates in an enlarged distal portion 40. Rotatably attached to the shaft 60 is a colpotomy cup 10. The colpotomy cup 10 has a rim 30 at its distal end, and a first electrode 31 on at least part of the rim 30. Tissue containment bag 20 is used with the colpotomy cup 10 during a TLH procedure. The tissue containment bag 20 has an opening 50 at one end. At least a portion of the opening 50 includes a second electrode 51. During a TLH procedure, the first and second electrodes 31 and 51 are respectively coupled to the terminals 202 and 204 of the electrosurgical energy generator (bipolar energy source) 200. Electrosurgical energy generators that produce a voltage potential between at least two electrodes so as to supply bipolar energy are well known, and thus the details of generator 200 are not further explained here. Suffice it to say that by disposing the electrodes 31 and 51 sufficiently close to each other (that is, on opposite (inside and outside) surfaces of the cervico-vaginal junction), and applying a suitable voltage potential between the electrodes 31 and 51, the tissue between the electrodes will be vaporized. By applying such energy around the entire circumference of the cervico-vaginal junction, the uterus will be detached.

In FIG. 1, the first electrode 31 is shown as completely encircling the rim 30 of the colpotomy cup 10 and the second electrode 51 is shown as completely encircling the opening 50 of the tissue containment bag 20. While such an arrangement is possible, it may not be preferred because a relatively large voltage potential will need to be applied between the two relatively large ring-shaped electrodes 31 and 51, which could be overly traumatic to the patient. Alternatively, if the supplied voltage is not enough, because the voltage will be applied over the entire surface area of each relatively large ring-shaped electrode 31/51, the applied power could be insufficient to completely vaporize enough tissue to fully detach the uterus. It is thus preferable to have at least one of the electrodes (usually the electrode provided with the cup) be relatively small such that it does not completely encircle the cervico-vaginal junction. In this case, the smaller electrode is moved around the cervico-vaginal junction during application of the electrosurgical energy so as to completely detach the uterus. Such an arrangement highly focuses the electrosurgical energy at a given area (corresponding to the small electrode) as the electrode is moved (rotated) around the cervico-vaginal junction. Embodiments that provide such an electrode arrangement will be described later.

Figure 2:
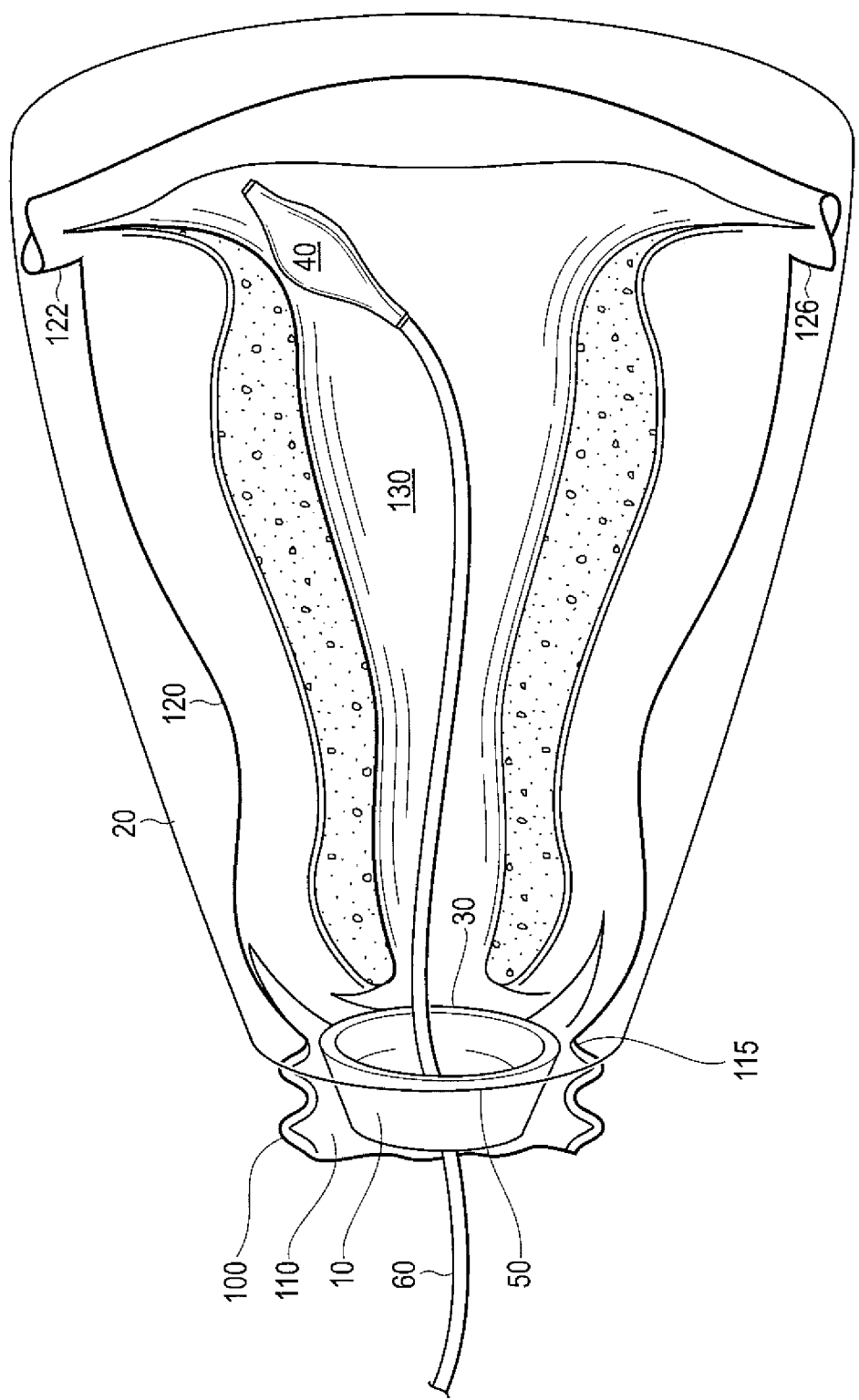
FIG. 2 shows a bipolar electrosurgical colpotomy device that incorporates a colpotomy cup and a tissue containment bag according to embodiments of the invention in position for resection.

FIG. 2 shows a bipolar electrosurgical colpotomy device that has been positioned to perform a uterine resection. The shaft 60 of the uterine manipulator, along with the colpotomy cup 10, is inserted trans-vaginally through the vaginal cavity 110. The shaft 60 is maneuvered so that the enlarged distal portion 40 is located within the uterus 130 and then is manipulated so that the uterus 130 is placed in a position desired by the surgeon. The colpotomy cup 10 is positioned by manipulating its own separate shaft (to be described later) so that the distal rim 30 of the colpotomy cup 10 is located at a patient's cervico-vaginal junction 115. The cervico-vaginal junction 115 is located where the vaginal wall 100 and uterine wall 120 meet. The tissue containment bag 20 is inserted laparoscopically, and, after detaching and clamping the uterine tubes 122 and 126 as is generally performed in TLH procedures, the bag 20 is located to surround the uterus 130, with the opening 50 of the tissue containment bag 20 aligned with the rim 30 of the colpotomy cup 10. Thus, the rim 30 of the colpotomy cup 10 is contacted with an internal surface of the patient's cervico-vaginal junction 115, whereas the opening 50 of the tissue containment bag 20 is positioned over and contacted with the external surface of the patient's cervico-vaginal junction.

The opening 50 of the tissue containment bag 20 typically has a size of about 15 cm-30 cm and/or could be elasticized so as to fit snuggly around the outer surface of the cervico-vaginal junction. The electrode 51 at the opening 50 of the bag 20 also could be elastic. More preferably, the bag opening 50 and the electrode 51 are flexible (but not necessarily elastic) and can be tightened like a noose around the uterus. Such an arrangement is easier for the surgeon to place over the uterus than an elastic opening/electrode, which might be difficult to place over the uterus.

Figure 11A:
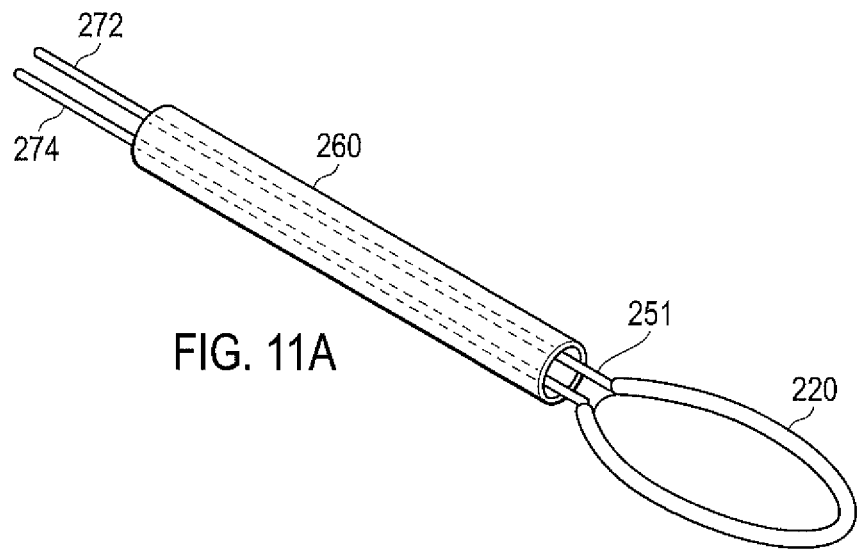
FIGS. 11A-11E show one way in which one embodiment of the tissue containment bag may be placed around a uterus to be resected.
Figure 11B:
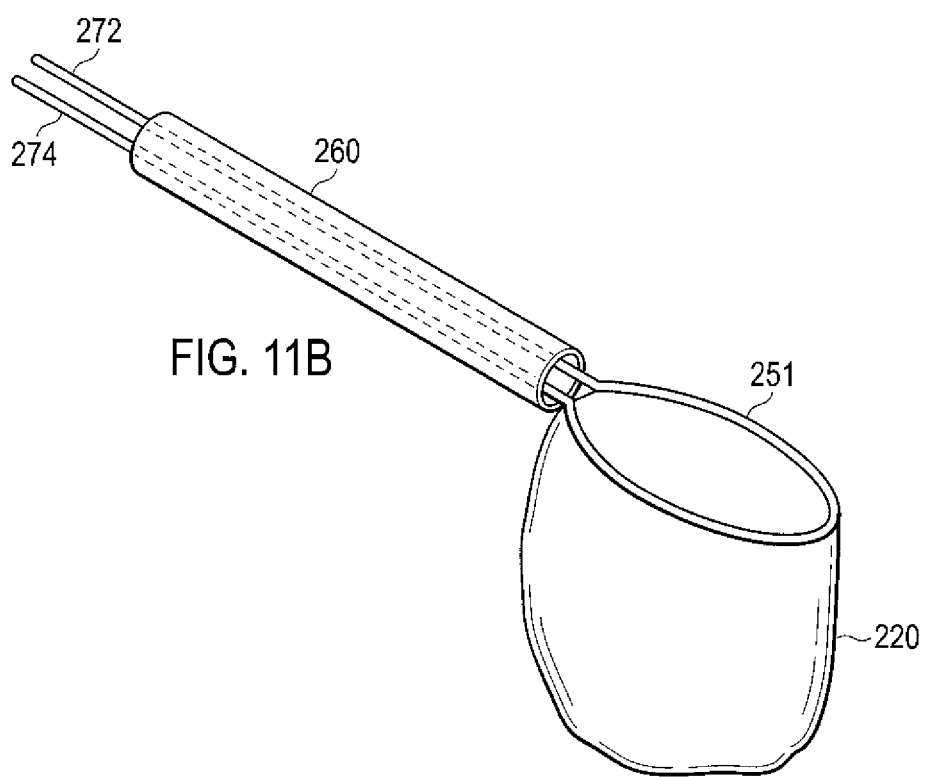
Figure 11C:
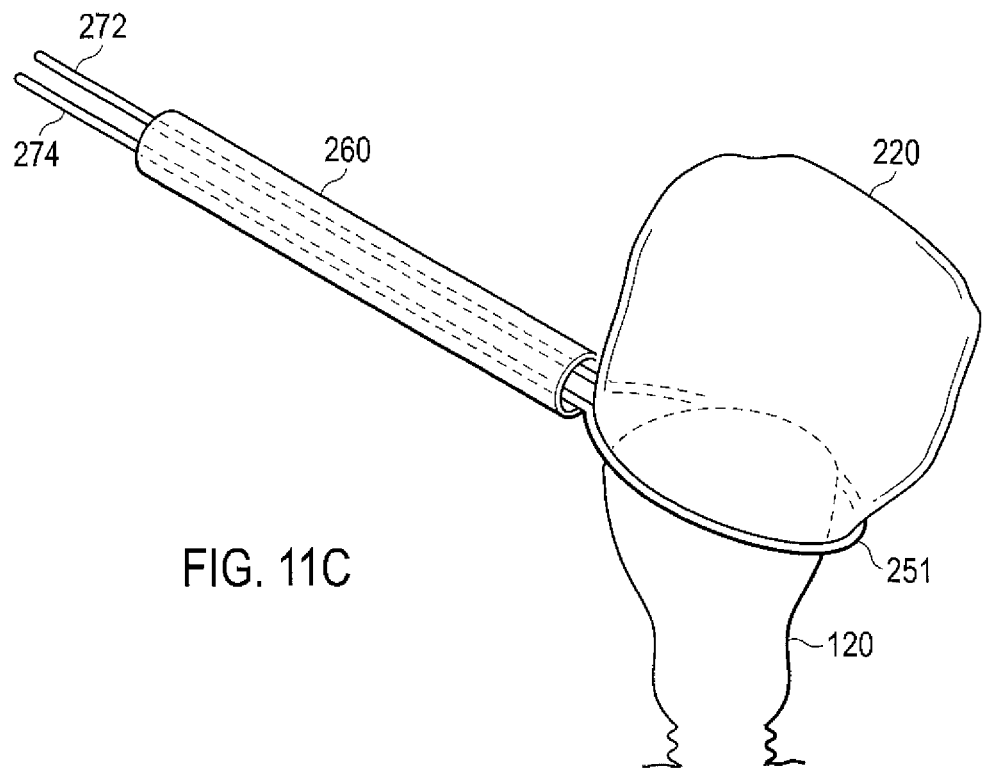
Figure 11D:
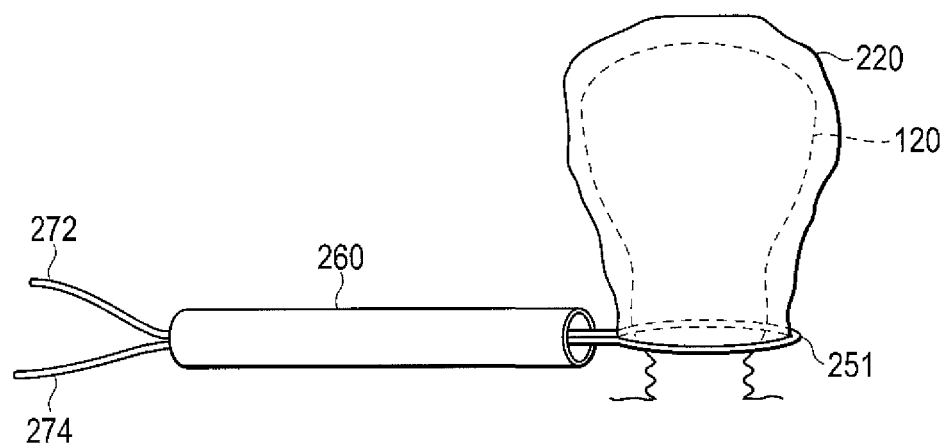
Figure 11E:
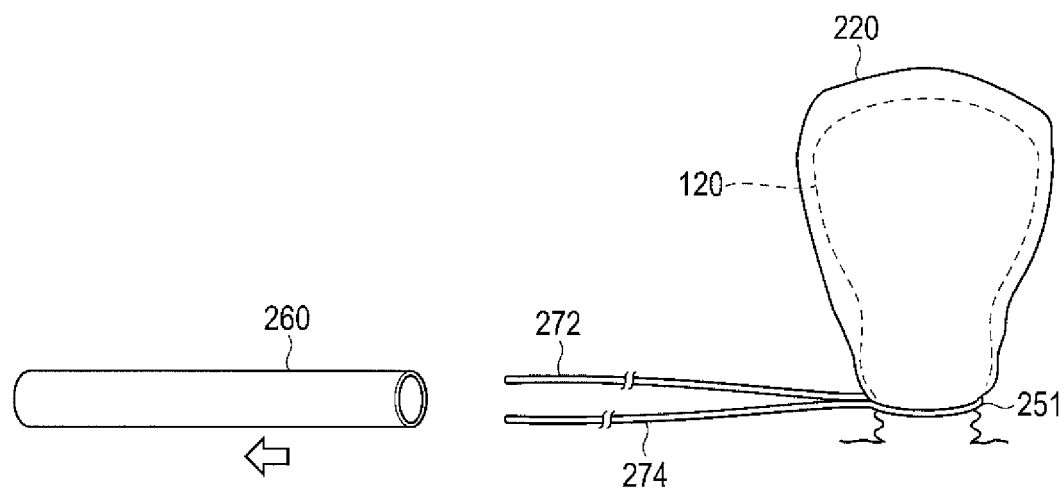

FIGS. 11A-11E show one way in which a tissue containment bag 220 having a large, non-elastic electrode 251 and bag opening can be placed over a uterus 120 and then tightened (or cinched) around the uterus before the uterus is resected. As shown in FIG. 11A, the electrode 251 is a wire having ends 272 and 274. The bag 220 has an opening that includes a passage through which the wire forming the electrode 251 is fed, similar to the way that a drawstring is fed through a passage in the waist of sweatpants, for example. The portion of the wire located in the opening will function as the electrode 251. The portions of the wire that will not function as the electrode (the portions including ends 272 and 274) may be covered by an insulator and are initially disposed at least partially within a protective tube 260, which is provided to make the device easier for the surgeon to manipulate. In FIG. 11A, the bag 220 is rolled-up around the portion of the wire forming the electrode 251 to reduce the overall size of the device for storage. FIG. 11B shows the bag 220 after the bag 220 has been deployed (e.g., unrolled) from the bag's stored state. FIG. 11C shows the bag 220 being placed over the uterus 120. FIG. 11D shows the bag 220 after it has been completely disposed over the uterus 120 but before the opening of the bag is tightened. As shown in FIG. 11E, after the protective tube 260 is removed, the ends 272 and 274 of the wire forming the electrode 251 are pulled so as to tighten the opening of the bag 220 around the uterus 120. The wire can be tied or otherwise secured (for example, clamped) in order to keep the bag opening and electrode 251 tightened against the uterus 120. Vaporization of uterine tissue by application of a voltage between the electrode 251 and the electrode 31 on the colpotomy cup then takes place as described previously.

After the uterus has been detached, it may be difficult to remove the bag 20 through the incision that was used to insert the bag 20. If so, then while still in the patient, a tissue cutting device could be inserted into the bag 20, for example, through the opening 50, in order to chop up (masticate) the tissue within the bag 20, thereby making it easier to remove the bag 20 with the masticated tissue therein through the incision.

Various embodiments of colpotomy cup designs usable in the invention now will be described in conjunction with FIGS. 3-10.

Figure 3:
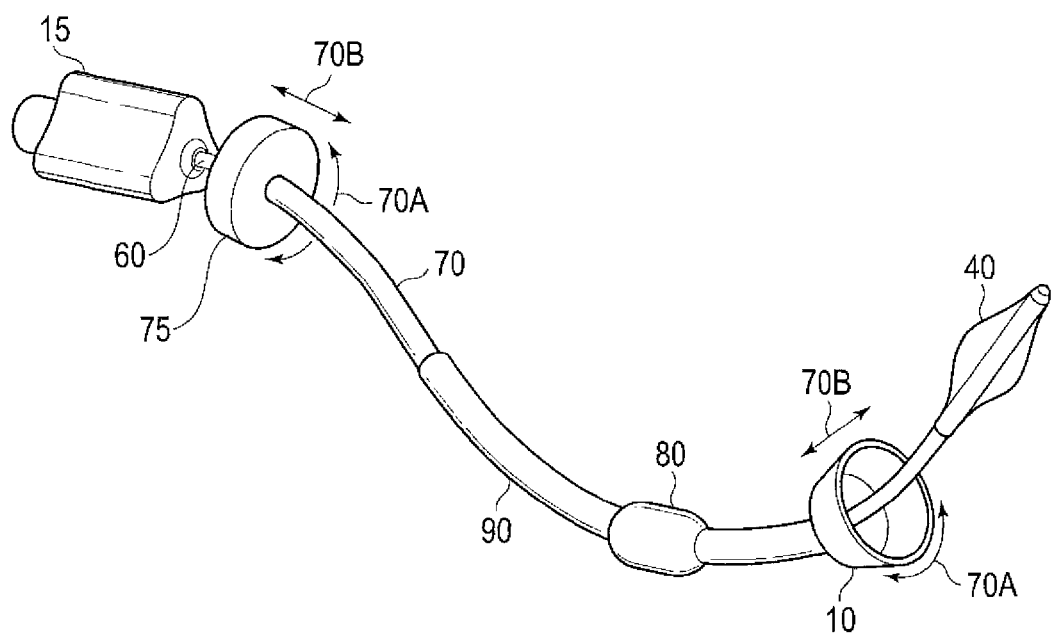
FIG. 3 illustrates a perspective view of an electrosurgical instrument that incorporates a colpotomy cup, uterine manipulator, and pneumoperitonial sealing device.

FIG. 3 illustrates a perspective view of an electrosurgical assembly including a colpotomy cup and uterine manipulator. The electrosurgical assembly includes a first (or inner) shaft 60, a second (or intermediate) shaft 70 and a third (or outer) shaft 90. The first shaft 60 is a uterine manipulator, with a handle 15 near its proximal end, and an enlarged distal portion 40. The first shaft 60 typically is rigid or semi-rigid and is used by the surgeon to position the uterus once the distal portion 40 is inserted into the uterus. The second shaft 70 carries the colpotomy cup 10 near its distal end, and a controller 75 near its proximal end. In an exemplary embodiment of the electrosurgical assembly, the controller 75 is capable of controlling the insertion and retraction of the second shaft 70 in direction 70B (the longitudinal direction) and rotation 70A around an axis of the second shaft 70 of the colpotomy cup 10. The third shaft 90 carries a seal 80 for maintaining pneumoperitoneum.

Figure 4:
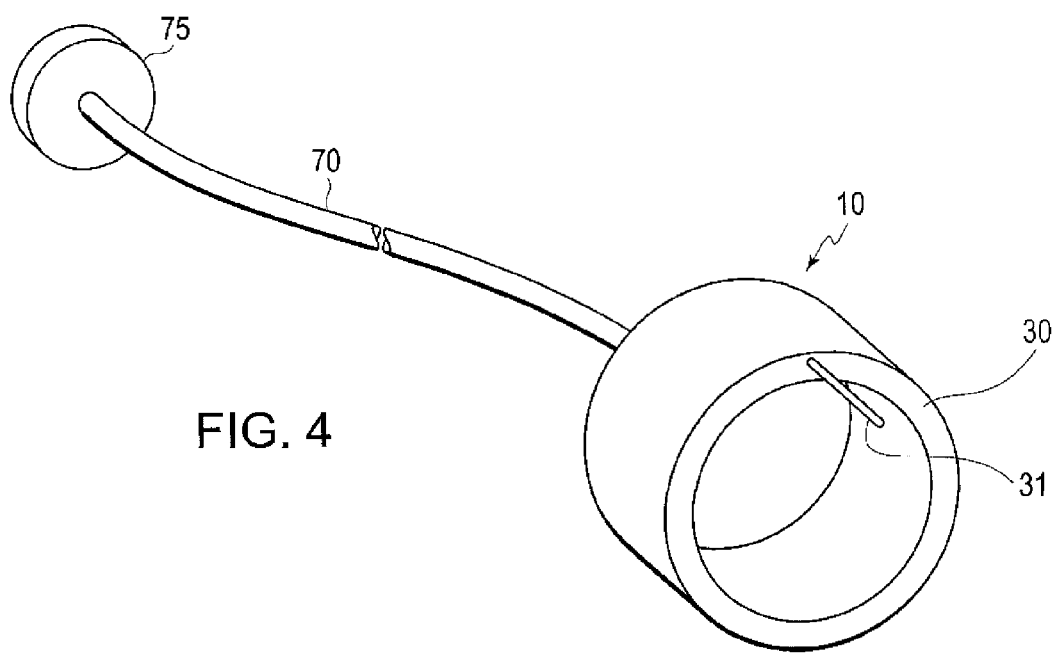
FIG. 4 illustrates a perspective view of the shaft bearing the colpotomy cup in an embodiment.

FIG. 4 illustrates a perspective view of the second shaft 70 of an exemplary embodiment of an electrosurgical assembly. The second shaft 70 has at its proximal end the controller 75 to manipulate the rotation and insertion and retraction of the second shaft including the colpotomy cup 10. In an embodiment according to FIG. 4, the first (active) electrode 31 is of a needle-type, and is placed on the distal rim 30 of the colpotomy cup 10. The needle is electrically conductive, but preferably has an insulative layer over its distal-most end. Thus the cutting energy will be applied from a base portion of the needle electrode 31 located proximal of the distal tip of the needle. Alternatively, the entire needle could be an exposed, electrically conductive member. The cutting signal is supplied to the electrode 31 through an electrically conductive conductor, such as a wire, that is incorporated into the second shaft 70. The proximal end of the second shaft 70 includes an electrical connection by which the conductor for the electrode 31 is attachable to an energy source.

Figure 5A:
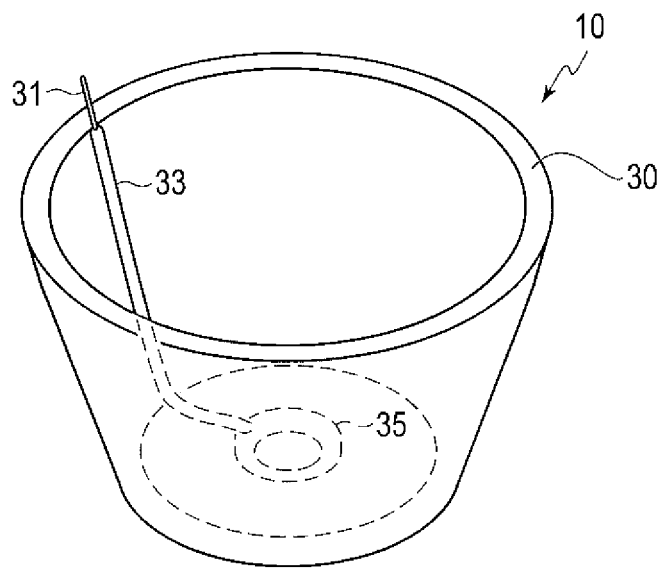
FIGS. 5A and 5B illustrate a perspective view and a plan view of a colpotomy cup and an active electrode that moves relative to the cup.
Figure 5B:
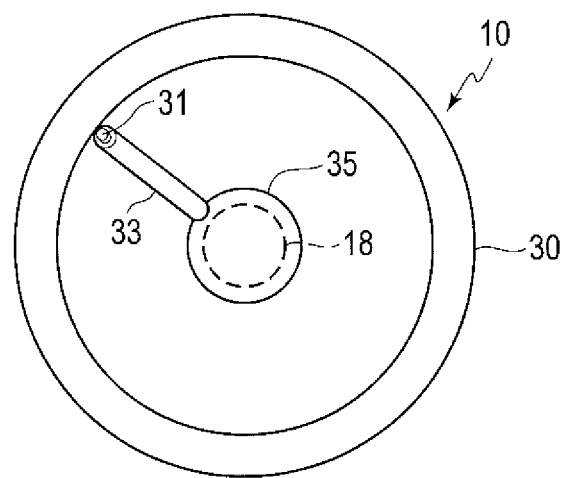

FIG. 5A illustrates a perspective view and FIG. 5B illustrates a plan view of an embodiment of the colpotomy cup 10 that can be provided on the second shaft 70. This embodiment disposes the first (active) electrode 31 at a distal end of an elongated portion 33 of a spindle 35 protruding from an aperture 18 in the proximal end of the colpotomy cup 10. When using this embodiment, the surgeon rotates the spindle 35 while cutting energy is supplied to the first electrode 31 so that the first electrode 31 performs and completes an incision by rotating 360° about the axis of the second shaft.

Figure 6:
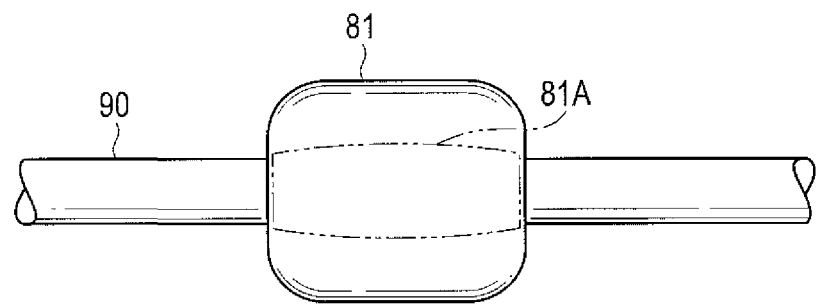
FIG. 6 illustrates a third shaft having a vaginal balloon that functions as a pneumoperitonial sealing device.
Figure 7:
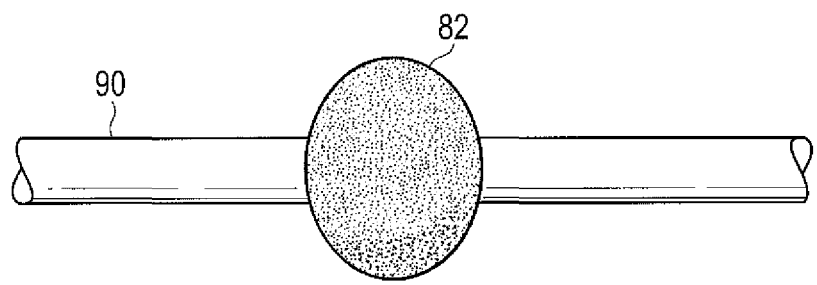
FIG. 7 illustrates a third shaft having a foam plug that functions as a pneumoperitonial sealing device.
Figure 8:
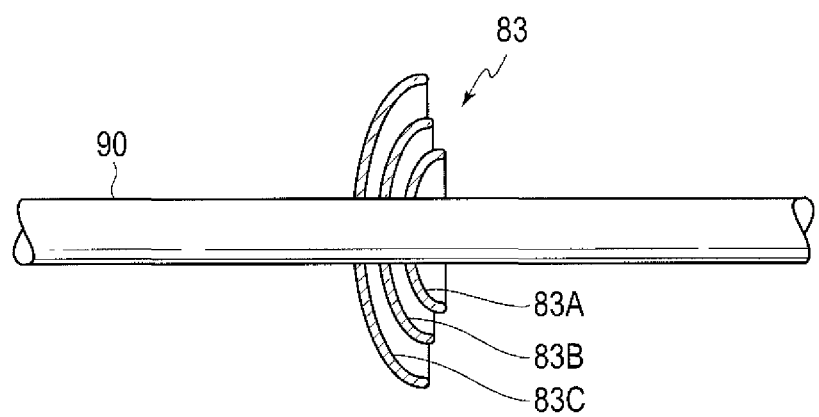
FIG. 8 illustrates a third shaft having a set of malleable discs that function as a pneumoperitonial sealing device.

FIGS. 6-8 illustrate different seals for maintaining pneumoperitoneum that may be located on the third shaft 90 in different embodiments of the invention. FIG. 6 illustrates an embodiment of the invention where the third shaft 90 includes a vaginal balloon 81 as the seal. An aspect of this embodiment of the seal is that the vaginal balloon can be in either a deflated state 81A or a fully inflated state 81, depending on the configuration that the physician desires. In another aspect of this embodiment, the third shaft 90 is slidably mounted over the second shaft and is capable of being positioned prior to inflation of the vaginal balloon 81. The third shaft includes a gas passage via which the balloon 81 can be inflated and deflated.

FIG. 7 illustrates an embodiment of the invention where the third shaft 90 includes a foam plug 82 as the seal. In an aspect of this embodiment, the third shaft 90 is slidably mounted over the second shaft and is capable of being positioned during surgery. The foam plug can be made of, for example, closed cell foam to form a soft malleable plug that is gas impermeable or an open cell foam with an external skin again making it gas impermeable. An important characteristic of the foam plug is to readily deflect for insertion without tissue injury and easy placement while subsequently conforming to the internal surface contours of the vaginal canal, in a manner so as to create the desired gas sealing or prevent the gas from leaking.

FIG. 8 illustrates an embodiment of the invention where the third shaft 90 includes malleable discs 83. The figure is illustrative and exhibits a configuration including three discs, 83A, 83B, and 83C. In an aspect of this embodiment, the malleable discs are configured so that the smallest disc, 83A, is the most distal. The discs increase in size in the proximal direction, with the most proximal, 83C, being the largest. The number, position, and size of the discs may be varied as required for a particular patient or application. The discs 83 are made of, for example, a soft malleable polymeric material or composite of materials such as LDPE or silicone that is gas impermeable. The malleability is critical for ease of insertion into the vaginal canal as well as limiting any tissue damage upon insertion and during placement.

Figure 9:
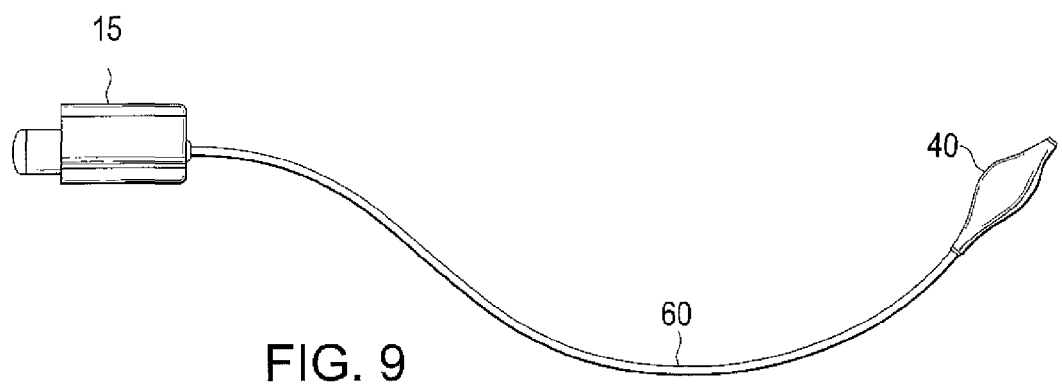
FIG. 9 illustrates a first shaft having a manipulator with an enlarged distal portion.

FIG. 9 illustrates an embodiment of the first shaft 60. In an aspect of this embodiment, a handle 15 for controlling the movement and orientation of the first shaft 60 is included near its proximal end. Also in this embodiment, an enlarged distal portion 40 is located near the distal end of the first shaft 60. The enlarged distal portion 40 of this embodiment may pass through the cervix, and enter the uterus for positioning of the uterus.

Figure 10:
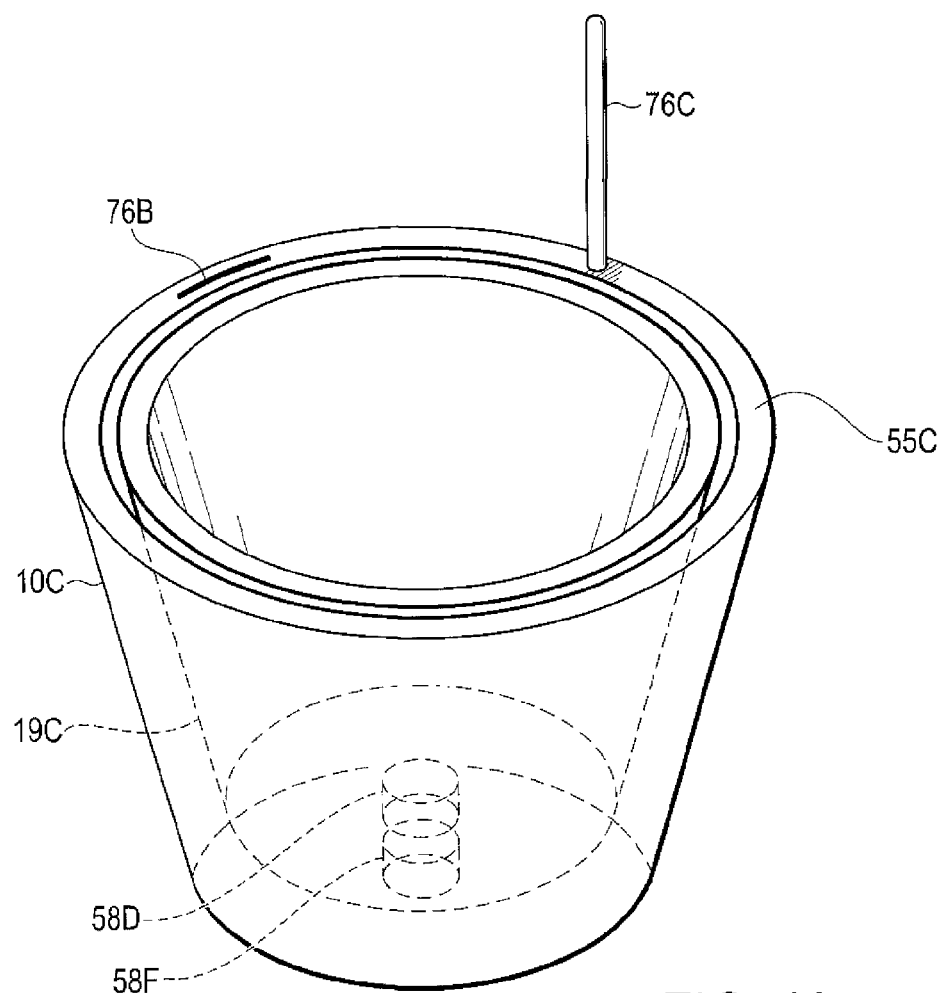
FIG. 10 illustrates a perspective, exploded view of a colpotomy cup with a rotating outer cup and a fixed inner cup.

FIG. 10 illustrates an embodiment of a colpotomy cup with a fixed inner cup 19C and a rotatable outer cup 10C. Fixed inner cup 19C has an aperture 58D at its proximal end, and rotatable outer cup 10C has an aperture 58F at its proximal end. In this embodiment, the fixed inner cup 19C is fixedly attached to the second shaft 70. The rotatable outer cup 10C is rotatably attached to the second shaft 70. The first electrode can take one of two forms. In the first form, the first electrode can be a portion 76B of the rim 55C of the rotatable outer cup 10C. Alternatively, the first electrode can be a needle electrode 76C placed on the rim 55C of the rotatable outer cup 10C. This embodiment performs the incision by rotating the rotatable outer cup 10C, while leaving the fixed inner cup 19C in a fixed position, while emitting energy from the first electrode 76B or 76C placed along the rim 55C of the rotatable outer cup 10C.

The illustrated exemplary embodiments are intended to be illustrative and not limiting. Various changes may be made without departing from the spirit and scope of the invention.

What is claimed is:

1. A bipolar electrosurgical colpotomy device comprising:
   a colpotomy cup that includes a proximal end, a distal end, a hollow portion at the distal end, a rim around the hollow portion at the distal end, and a first electrode located adjacent to the rim, the rim being configured to contact an internal surface of a patient's cervico-vaginal junction; and
   a bag configured to contain tissue, the bag having a closed end and an open end that defines an opening, the bag including a second electrode located adjacent to the opening, the bag being configured to surround the patient's uterus and the opening being configured to fit over an external surface of the patient's cervico-vaginal junction,
   wherein the first and second electrodes are configured to vaporize tissue at the patient's cervico-vaginal junction by electrosurgical energy passing through the tissue disposed between the first and second electrodes upon application of a voltage potential between the first and second electrodes.

2. The bipolar electrosurgical colpotomy device according to claim 1, wherein the second electrode completely encircles the opening of the bag.

3. The bipolar electrosurgical colpotomy device according to claim 1, wherein the first electrode completely encircles the rim of the colpotomy cup.

4. The bipolar electrosurgical colpotomy device according to claim 1, further comprising:
   a first shaft having a proximal end, a distal end and a uterine manipulator adjacent to the distal end of the first shaft; and
   a second shaft disposed over the first shaft and having a proximal end and a distal end, the proximal end of the colpotomy cup being attached to the distal end of the second shaft so that the colpotomy cup moves with the second shaft.

5. The bipolar electrosurgical colpotomy device according to claim 4, wherein the second shaft is rotatable around the first shaft.

6. The bipolar electrosurgical colpotomy device according to claim 5, wherein the first electrode is located adjacent to only a portion of the rim such that the second shaft and attached colpotomy cup must be rotated around the first shaft in order to completely detach the uterus.

7. The bipolar electrosurgical colpotomy device according to claim 4, further comprising a spindle to which the first electrode is attached, the spindle being rotatable about an axis of the second shaft independently of the colpotomy cup.

8. The bipolar electrosurgical colpotomy device according to claim 1, further comprising a spindle to which the first electrode is attached, the spindle being rotatable about an axis of the colpotomy cup.

9. The bipolar electrosurgical colpotomy device according to claim 1, further comprising a second colpotomy cup disposed within the colpotomy cup, the colpotomy cup and the attached first electrode being rotatable relative to the second colpotomy cup.

* * * * *